(12) United States Patent
Faram

(10) Patent No.: US 8,051,854 B2
(45) Date of Patent: Nov. 8, 2011

(54) CONTINUOUS HIGH-FREQUENCY OSCILLATION BREATHING TREATMENT APPARATUS

(75) Inventor: Joseph Dee Faram, Dallas, TX (US)

(73) Assignee: Comedica Incorporated, Dallas, TX (US)

( * ) Notice: Subject to any disclaimer, the term of this patent is extended or adjusted under 35 U.S.C. 154(b) by 1089 days.

(21) Appl. No.: 11/855,765

(22) Filed: Sep. 14, 2007

(65) Prior Publication Data

US 2008/0066754 A1    Mar. 20, 2008

Related U.S. Application Data

(60) Provisional application No. 60/825,864, filed on Sep. 15, 2006.

(51) Int. Cl.
  A62B 7/00 (2006.01)
  A62B 9/00 (2006.01)
  A61M 11/00 (2006.01)
(52) U.S. Cl. .............................. 128/204.25; 128/200.14
(58) Field of Classification Search ............ 128/200.14, 128/200.24, 203.12, 203.14, 204.18, 204.25, 128/205.19
  See application file for complete search history.

(56) References Cited

U.S. PATENT DOCUMENTS

| | | | |
|---|---|---|---|
| 402,779 A | 5/1889 | Steinhoff |
| 1,150,238 A | 8/1915 | Winbray |
| 3,068,856 A | 12/1962 | Bird at al. |
| 3,083,707 A | 4/1963 | Seeler |
| 3,291,122 A | 12/1966 | Engstrom et al. |
| 3,301,255 A | 1/1967 | Thompson |
| 3,537,448 A | 11/1970 | Liston |
| 3,561,444 A | 2/1971 | Boucher |
| 3,584,621 A | 6/1971 | Bird et al. |
| 3,630,196 A | 12/1971 | Bird et al. |
| 3,664,337 A | 5/1972 | Lindsey et al. |
| 3,861,386 A | 1/1975 | Harris et al. |
| 4,054,134 A | 10/1977 | Kritzer |
| 4,062,358 A | 12/1977 | Kritzer |
| 4,182,599 A | 1/1980 | Eyrick et al. |
| 4,195,044 A | 3/1980 | Miller |
| 4,245,633 A | 1/1981 | Erceg |
| 4,263,907 A | 4/1981 | Lindsey |
| 4,436,090 A | 3/1984 | Darling |
| 4,471,773 A | 9/1984 | Bunnell et al. |
| 4,558,710 A | 12/1985 | Eichler |
| 4,601,465 A | 7/1986 | Roy |
| 4,635,857 A | 1/1987 | Hughes |
| 4,747,402 A | 5/1988 | Reese et al. |
| 4,770,164 A | 9/1988 | Lach et al. |
| 4,823,784 A | 4/1989 | Bordoni et al. |

(Continued)

OTHER PUBLICATIONS

A Manual on VDR—Volumetric Diffusive Repiration (VDR)—The VDR-4 Percussionator for the Most Challenging Patients Requiring Mechanical Cardiopulmonary Care-Percussionaire Corporation, Idaho, Copyright 1996 (75 pages).

(Continued)

Primary Examiner — Kristen Matter
(74) Attorney, Agent, or Firm — Barnes & Thornburg LLP

(57) ABSTRACT

A continuous high-frequency oscillation breathing device delivers therapy during both inhalation and exhalation in order to assist in clearing secretions from the lungs. A venturi patient interface circuit is combined with medicated aerosol to deliver continuous high-frequency oscillation therapy. Fixed open apertures in the patient interface circuit allow ingress and egress of flow, and are calibrated to allow exhalation and prevent stacking of successive breaths.

16 Claims, 5 Drawing Sheets

U.S. PATENT DOCUMENTS

| | | |
|---|---|---|
| 4,867,151 A | 9/1989 | Bird |
| 4,951,659 A | 8/1990 | Weiler et al. |
| 4,964,404 A | 10/1990 | Stone |
| 4,973,047 A | 11/1990 | Norell |
| 4,981,295 A | 1/1991 | Belman et al. |
| 5,018,517 A | 5/1991 | Liardet |
| 5,027,809 A | 7/1991 | Robinson |
| 5,067,707 A | 11/1991 | Køhnke |
| 5,069,449 A | 12/1991 | Wardwell |
| 5,107,830 A | 4/1992 | Younes |
| 5,127,400 A | 7/1992 | DeVries et al. |
| 5,150,291 A | 9/1992 | Cummings et al. |
| 5,193,529 A | 3/1993 | Labaere |
| 5,261,394 A | 11/1993 | Mulligan et al. |
| 5,277,175 A | 1/1994 | Riggs et al. |
| 5,322,057 A | 6/1994 | Raabe et al. |
| 5,355,873 A | 10/1994 | Del Bon et al. |
| 5,390,665 A | 2/1995 | Leach |
| 5,398,676 A | 3/1995 | Press et al. |
| 5,413,110 A | 5/1995 | Cummings et al. |
| 5,415,161 A | 5/1995 | Ryder |
| 5,423,313 A | 6/1995 | Olsson et al. |
| 5,439,430 A | 8/1995 | Rubens et al. |
| 5,451,190 A | 9/1995 | Liardet |
| 5,479,920 A | 1/1996 | Piper et al. |
| 5,535,738 A | 7/1996 | Estes et al. |
| 5,542,416 A | 8/1996 | Chalvignac |
| 5,547,440 A | 8/1996 | Rubens et al. |
| 5,570,682 A | 11/1996 | Johnson |
| 5,598,839 A | 2/1997 | Niles et al. |
| 5,617,844 A | 4/1997 | King |
| 5,617,847 A | 4/1997 | Howe |
| 5,664,562 A | 9/1997 | Bourdon |
| 5,666,945 A | 9/1997 | Davenport |
| 5,694,919 A | 12/1997 | Rubsamen et al. |
| 5,713,349 A | 2/1998 | Keaney |
| 5,823,179 A | 10/1998 | Grychowski et al. |
| 5,829,429 A | 11/1998 | Hughes |
| 5,906,198 A | 5/1999 | Flickinger |
| 5,937,857 A | 8/1999 | Caterini et al. |
| 5,938,117 A | 8/1999 | Ivri |
| 5,950,619 A | 9/1999 | Van Der Linden et al. |
| 5,964,223 A | 10/1999 | Baran |
| 5,970,974 A | 10/1999 | Van Der Linden et al. |
| 6,044,841 A | 4/2000 | Verdun et al. |
| 6,058,932 A | 5/2000 | Hughes |
| 6,076,519 A | 6/2000 | Johnson |
| 6,076,520 A | 6/2000 | Cooper |
| 6,079,413 A | 6/2000 | Baran |
| 6,085,740 A | 7/2000 | Ivri et al. |
| 6,085,746 A | 7/2000 | Fox |
| 6,116,233 A | 9/2000 | Denyer et al. |
| 6,167,881 B1 | 1/2001 | Hughes |
| 6,210,345 B1 | 4/2001 | Van Brunt |
| 6,234,167 B1 | 5/2001 | Cox et al. |
| 6,240,919 B1 | 6/2001 | MacDonald et al. |
| 6,269,810 B1 | 8/2001 | Brooker et al. |
| 6,289,892 B1 | 9/2001 | Faithfull et al. |
| 6,302,105 B1 | 10/2001 | Wickham et al. |
| 6,336,455 B1 | 1/2002 | Howlett |
| 6,340,025 B1 | 1/2002 | Van Brunt |
| 6,355,002 B1 | 3/2002 | Faram et al. |
| 6,363,932 B1 | 4/2002 | Forchione et al. |
| 6,402,046 B1 | 6/2002 | Loser |
| 6,405,934 B1 | 6/2002 | Hess et al. |
| 6,412,481 B1 | 7/2002 | Bienvenu et al. |
| 6,415,791 B1 | 7/2002 | Van Brunt |
| 6,425,393 B1 | 7/2002 | Lurie et al. |
| 6,427,690 B1 | 8/2002 | McCombs et al. |
| 6,435,175 B1 | 8/2002 | Stenzler |
| 6,450,163 B1 | 9/2002 | Blacker et al. |
| 6,467,476 B1 | 10/2002 | Ivri et al. |
| 6,526,976 B1 | 3/2003 | Baran |
| 6,540,153 B1 | 4/2003 | Ivri |
| 6,540,154 B1 | 4/2003 | Ivri et al. |
| 6,546,927 B2 | 4/2003 | Litherland et al. |
| 6,550,472 B2 | 4/2003 | Litherland et al. |
| 6,550,476 B1 | 4/2003 | Ryder |
| 6,557,549 B2 | 5/2003 | Schmidt et al. |
| 6,568,387 B2 | 5/2003 | Davenport et al. |
| 6,571,790 B1 | 6/2003 | Weinstein |
| 6,581,596 B1 | 6/2003 | Truitt et al. |
| 6,581,598 B1 | 6/2003 | Foran et al. |
| 6,581,600 B2 | 6/2003 | Bird |
| 6,588,421 B1 | 7/2003 | Diehl et al. |
| 6,588,422 B1 | 7/2003 | Berthon-Jones et al. |
| 6,595,203 B1 | 7/2003 | Bird |
| 6,598,602 B1 | 7/2003 | Sjoholm |
| 6,598,603 B1 | 7/2003 | Andersson et al. |
| 6,609,517 B1 | 8/2003 | Estes et al. |
| 6,612,303 B1 | 9/2003 | Grychowski et al. |
| 6,615,831 B1 | 9/2003 | Tuitt et al. |
| 6,626,175 B2 | 9/2003 | Jafari et al. |
| 6,631,721 B1 | 10/2003 | Salter et al. |
| 6,640,806 B2 | 11/2003 | Yurko |
| 6,644,304 B2 | 11/2003 | Grychowski et al. |
| 6,644,310 B1 | 11/2003 | Delache et al. |
| 6,644,311 B1 | 11/2003 | Truitt et al. |
| 6,663,574 B2 | 12/2003 | Faram et al. |
| 6,679,258 B1 | 1/2004 | Strom |
| 6,694,969 B1 | 2/2004 | Heinonen et al. |
| 6,702,998 B2 | 3/2004 | Conner |
| 6,708,688 B1 | 3/2004 | Rubin et al. |
| 6,718,969 B1 | 4/2004 | Rubin et al. |
| 6,722,362 B2 | 4/2004 | Hete et al. |
| 6,729,327 B2 | 5/2004 | McFarland, Jr. |
| 6,729,334 B1 | 5/2004 | Baran |
| 6,737,042 B2 | 5/2004 | Rabinowitz et al. |
| 6,752,151 B2 | 6/2004 | Hill |
| 6,776,159 B2 | 8/2004 | Pelerossi et al. |
| 6,805,118 B2 | 10/2004 | Brooker et al. |
| 6,805,120 B1 | 10/2004 | Jeffrey et al. |
| 6,823,866 B2 | 11/2004 | Jafari et al. |
| 6,848,443 B2 | 2/2005 | Schmidt et al. |
| 6,851,425 B2 | 2/2005 | Jaffre et al. |
| 6,854,462 B2 | 2/2005 | Berthon-Jones et al. |
| 6,880,556 B2 | 4/2005 | Uchiyama et al. |
| 6,904,906 B2 | 6/2005 | Salter et al. |
| 6,907,881 B2 | 6/2005 | Suki et al. |
| 6,910,479 B1 | 6/2005 | Van Brunt |
| 6,915,803 B2 | 7/2005 | Berthon-Jones et al. |
| 6,932,084 B2 | 8/2005 | Estes et al. |
| 6,948,497 B2 | 9/2005 | Zdrojkowski et al. |
| 6,968,840 B2 | 11/2005 | Smith et al. |
| 7,011,091 B2 | 3/2006 | Hill et al. |
| 7,013,894 B2 | 3/2006 | McFarland, Jr. |
| 7,036,500 B2 | 5/2006 | Niles et al. |
| 7,059,324 B2 | 6/2006 | Pelerossi et al. |
| 7,066,176 B2 | 6/2006 | Jaffe et al. |
| 7,070,761 B2 | 7/2006 | Rabinowitz et al. |
| 7,077,133 B2 | 7/2006 | Yagi et al. |
| 7,100,607 B2 | 9/2006 | Zdrojkowski et al. |
| 7,128,069 B2 | 10/2006 | Farrugia et al. |
| 7,131,439 B2 | 11/2006 | Blacker et al. |
| 7,165,547 B2 | 1/2007 | Truitt et al. |
| 7,188,621 B2 | 3/2007 | DeVries et al. |
| 7,191,776 B2 | 3/2007 | Niles et al. |
| 7,191,780 B2 | 3/2007 | Faram |
| 7,204,245 B2 | 4/2007 | Johnson et al. |
| 7,210,480 B2 | 5/2007 | Lurie et al. |
| 7,232,417 B2 | 6/2007 | Plante |
| 7,302,949 B2 | 12/2007 | Pelerossi et al. |
| 7,445,607 B2 | 11/2008 | Plante |
| 7,469,700 B2 | 12/2008 | Baran |
| 7,472,702 B2 | 1/2009 | Beck et al. |
| 7,472,705 B2 | 1/2009 | Baran |
| 7,500,481 B2 | 3/2009 | Delache et al. |
| 7,562,657 B2 | 7/2009 | Blanch et al. |
| 7,600,511 B2 | 10/2009 | Power et al. |
| 7,699,054 B2 | 4/2010 | Pelerossi et al. |
| 2003/0051731 A1 | 3/2003 | Be'eri et al. |
| 2003/0140921 A1 | 7/2003 | Smith et al. |
| 2003/0140925 A1 | 7/2003 | Sapienza et al. |
| 2003/0145849 A1 | 8/2003 | Drinan et al. |
| 2003/0183226 A1 | 10/2003 | Brand et al. |
| 2003/0205229 A1 | 11/2003 | Crockford et al. |
| 2005/0061318 A1* | 3/2005 | Faram ..................... 128/204.18 |

| | | |
|---|---|---|
| 2005/0109340 A1 | 5/2005 | Tehrani |
| 2005/0150489 A1 | 7/2005 | Dunfield et al. |
| 2005/0165334 A1 | 7/2005 | Lurie |
| 2005/0172954 A1 | 8/2005 | Smith et al. |
| 2005/0217666 A1 | 10/2005 | Fink et al. |
| 2006/0144398 A1 | 7/2006 | Doshi et al. |
| 2006/0178245 A1 | 8/2006 | Schiller et al. |
| 2006/0201500 A1 | 9/2006 | Von Hollen et al. |
| 2006/0243274 A1 | 11/2006 | Lieberman et al. |
| 2006/0272642 A1 | 12/2006 | Chalvignac |
| 2007/0017522 A1 | 1/2007 | Be-Eri et al. |
| 2007/0017523 A1 | 1/2007 | Be-Eri et al. |
| 2007/0089740 A1 | 4/2007 | Baumert et al. |
| 2007/0186928 A1 | 8/2007 | Be-Eri |
| 2008/0000475 A1 | 1/2008 | Hill |
| 2008/0000477 A1 | 1/2008 | Huster et al. |
| 2008/0015456 A1 | 1/2008 | McCawley et al. |
| 2008/0091117 A1 | 4/2008 | Choncholas et al. |
| 2008/0190429 A1 | 8/2008 | Tatarek |
| 2008/0283060 A1 | 11/2008 | Bassin |
| 2009/0020121 A1 | 1/2009 | Bassin |

OTHER PUBLICATIONS

Bird Demand CPAP, Bird Technical Information Manual, Copyright 1977 Bird Corp. (138 pages).

The Percussionaire Gold Edition IPV-1S(r) Universal Percussionator—Form 33120 Percusionaire Corporation, Idaho (2 pages).

The Basic Institutional Intrapulmonary Percussionator—Percussionaire Model IPV-1—Percussionaire Corporation, Idaho (2 pages).

The Bird—Instructor Reference Manual by Forrest M. Bird for the Bird Institute of Respiratory Technology,Apr. 1976 (14 pages).

Organization and Set Up of the Percussive VDR Intensive Care Breathing Circuit VDR Failsafe Breathing Circuit for Intensive Care—Percussionaire Corporation, Idaho (31 pages).

Intrapulmonary Percussive Ventilation IPV Discussion paper, Copyright Percussionaire 2000 (30 pages).

Specifications for Spanker Respirators, Copyright Percussionaire 1985 (6 pages).

Percussionaire Product Sheet, Dec. 12, 2002 (2 pages).

IPV-1C Institutional Intrapulmonary Percussionator spec., by Percussionaire Oct. 28, 2001 (2 pages).

IPV Users Manual, Copyright Percussionaire Dec. 1, 2000 (48 pages).

Letter dated Nov. 12, 2009 with enclosed Response dated Feb. 6, 2009 (80 pages).

* cited by examiner

CONTINUOUS HIGH-FREQUENCY OSCILLATION BREATHING TREATMENT APPARATUS

CROSS-REFERENCE TO RELATED APPLICATION

This application claims the benefit of priority from U.S. Provisional Application No. 60/825,864 filed on Sep. 15, 2006.

FIELD OF THE INVENTION

The invention relates to a therapeutic breathing device which delivers continuous high-frequency oscillation therapy during both inhalation and exhalation to facilitate the removal of mucus secretions from the lungs.

BACKGROUND OF THE INVENTION

Healthy people are able to clear mucus secretions from their lungs by means of bi-directional airflow and a system of tiny hairlike follicles called "mucociliary escalators." Airflow passing over the secretions creates shear forces that combine with the mucociliary escalators to transport mucus from the lower respiratory tract to upper airways. From there the secretions can be removed by coughing.

However, during illness a person's normal ability to remove secretions may become impaired. As the natural secretion clearance mechanism becomes more challenged, secretions may build up in the lungs, bronchial and tracheal passages creating a heightened potential for further exacerbation of illness. Retained mucus secretions in the warm, moist environment of the lungs create an excellent opportunity for the growth of bacteria. In addition, retained secretions may hinder the lungs' ability to exchange gas and increase the risk of pulmonary neoplasm. Keeping the lungs open and clear of secretions is integral to maintaining a healthy defense of the pulmonary system.

As the population ages, and the quality of air decreases, assaults on the respiratory system continue to rise. In addition to curable pulmonary infections, there are some 16 million people in the United States alone diagnosed with chronic lung disease, and it is estimated that an additional 16 million cases go undiagnosed. Associated costs in both healthcare and lost production hours are staggering.

Because of the rising costs associated with pulmonary disease and the importance of keeping the lungs clear, clinicians and patients alike seek simple, inexpensive therapy devices that can enhance secretion mobilization. However, despite the variety of devices available, few show evidence of overall benefit.

In the late 1970's a Swedish anesthesiologist pioneered the use of "high-frequency ventilation" for life support by programming a ventilator to deliver 60 breaths per minute, or 1 hertz. Subsequently the application of high-frequency delivery of gas to the airways was found to show favorable results in mobilizing secretions, especially when combined with medicated aerosol. While exact mechanisms of this therapy are not fully understood, it is likely that, as the column of air in the airways is oscillated by the high-frequency pulses of gas, the viscosity of the mucus is reduced by the untangling of some of the larger molecule strands, such as DNA and F-actin, which tend to be present as a byproduct of infection. Additionally, the high-frequency, intermittent delivery of gas contributes to a bi-directional flow creating wind shear forces which, in turn, help to mobilize the secretions in a cephalad fashion. However, in spite of therapeutic promise, the vast majority of those in need of this therapy do not have access to it because current technology is too complex and, therefore, ultimately too expensive.

U.S. Pat. Nos. 4,592,349, 4,805,613, 4,838,260, 4,930,501, 5,007,420, 5,116,088, 5,165,398, and 5,862,802 describe ventilators that combine high-frequency oscillation gas flow with aerosol. However, because these ventilators are designed primarily for life support, they connect to the patient via patient adapters that incorporate relatively complex mechanized valves that open and close between phasic shifts from inhalation to exhalation.

U.S. Pat. No. 4,592,349 describes a "pneumatic clutching means" as an exhalation valve assembly with a venturi slidably mounted within in such a way as to move between open and closed positions. Although highly effective in delivering life-support ventilation, the sliding venturi patient adapter is too complex, bulky, and costly to manufacture to be included in a simple, inexpensive therapy device. The patient interface necessitates the fabrication of a number of moving parts made of a variety of materials. The resulting friction of the constant sliding between open and closed positions eventually fatigues valve components that must be replaced. Additionally, the sliding venturi patient interface requires critical dimensions that prevent a reduction in its size and weight.

Although an alternate embodiment of a patient adaptor to be used with the above devices described in U.S. Pat. No. 4,592,349 utilizes a fixed venturi, it, nonetheless, must incorporate or attach to a mechanical exhalation valve that opens and closes between inhalation and exhalation. This design, again, although effective in delivering life-support ventilation, renders the patient connector too complex and costly to be used in a simple, inexpensive breathing therapy device.

In addition to being expensive because of their complexity of manufacturing and maintenance, the devices currently capable of delivering high-frequency oscillatory therapy to the lungs are complicated and difficult to use. They require either significant training of the patient or a trained professional to administer the therapy. U.S. Pat. No. 4,592,349, cited above, also describes a simpler version of these life-support ventilators which is specifically intended for therapeutic use. However, even this simpler, scaled-down version is designed with a mechanism to terminate the delivery of gas during exhalation, as well as adjustments for both pressure and pulse frequency during a therapy session. This design renders the device both costly to manufacture and complex to use.

SUMMARY OF THE INVENTION

The present invention is an apparatus for delivering continuous high-frequency oscillation therapy to the lungs during both inhalation and exhalation in order to assist in mucus secretion clearance. The invention relates to the patient interface of a system which also would typically include a pressurized gas source, a pressure reduction regulator, a flow interrupter, and a nebulizer.

Accordingly, an object of the present invention is to provide a continuous high-frequency oscillation breathing treatment device that can be manufactured simply and inexpensively.

Another object of the invention is to provide a continuous high-frequency oscillation breathing treatment device that is sufficiently simple to use so that it requires little or no training.

Another object of the present invention is to provide a continuous high-frequency oscillation breathing treatment device that delivers pulses to the patient and allows the patient to exhale into it without stacking successive volumes of gas in the airways.

Another object of the invention is to provide a continuous high-frequency oscillation breathing treatment device that will be simple and inexpensive to maintain.

Another object of the invention is to provide a continuous high-frequency oscillation breathing treatment device that maximizes safety during use.

Another object of the invention is to provide a continuous high-frequency oscillation breathing treatment device that is sufficiently small and lightweight enough to be conveniently transported.

Another object of the invention is to provide a continuous high-frequency oscillation breathing treatment device with unitary construction of the body of the patient interface.

Another object of the invention is to provide a continuous high-frequency oscillation breathing treatment device that integrates a pressure monitoring orifice.

Another object of the present invention is to provide a continuous high-frequency oscillation breathing treatment device comprising a patient interface which in turn comprises a fixed venturi.

BRIEF DESCRIPTIONS OF THE DRAWINGS

DETAILED DESCRIPTION

Figure 1:
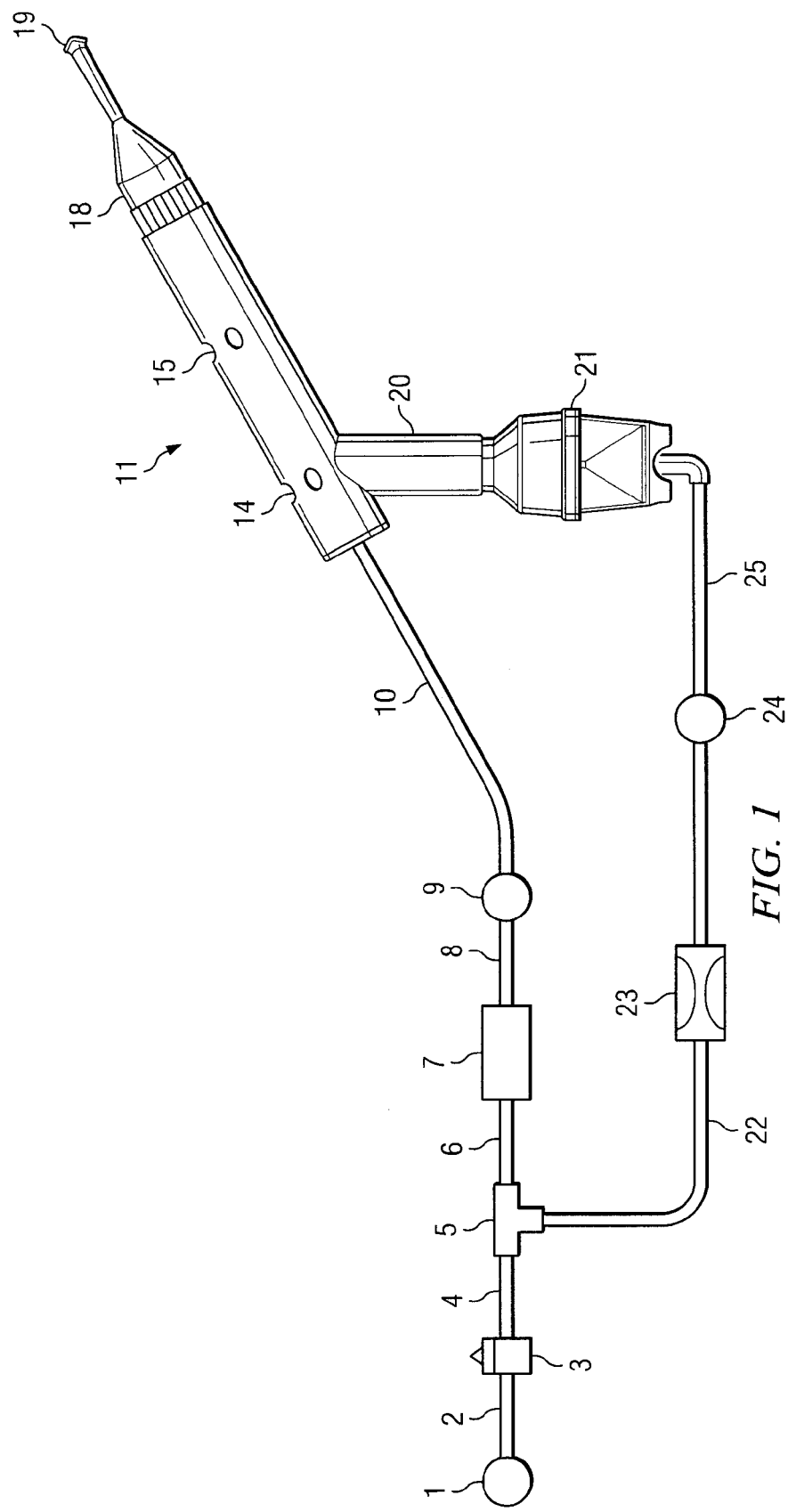
FIG. 1 is a schematic representation of the continuous high-frequency oscillation breathing therapy apparatus of present invention.

FIG. 1 shows a schematic diagram of a continuous high-frequency oscillation breathing treatment apparatus comprising a source of pressurized gas attached to a source gas 1, a gas supply tube 2, a reduction regulator 3, a flow interrupter valve 7, and a patient interface circuit comprised of circuit tubes 10 and 25, a breathing head assembly 11 and a nebulizer 21. Source gas 1 connects to pressure reduction regulator 3 by means of a source gas supply tube 2. Pressure reduction regulator 3 is connected via a bore tube 4 to splitting connector 5. Bore tube 4 is preferably a small bore (⅛" ID) tube, but as one skilled in the art will appreciate other dimensions may be used and remain within the scope and spirit of the invention. One end of splitting connector 5 attaches to tube 22 and the other end of splitting connector 5 attaches to tube 6.

Tube 22 connects to, or is integral with, reducing orifice 23, which in turn connects to circuit connector 24. Circuit tube 25 connects by one end to circuit connector 24 and by the other end to nebulizer 21.

Tube 6 connects by one end to splitting connector 5 and by the other end to flow interrupter valve 7, for example, a pneumatic "logic cell cartridge", model A50146, manufactured by Percussionaire Corp. The other end of flow interrupter valve 7 is connected to tube 8 which connects to circuit connector 9. Circuit connector 9 connects to one end of circuit tube 10, and the other end of circuit tube 10 connects to the rearmost end of breathing head assembly 11.

Figure 2:
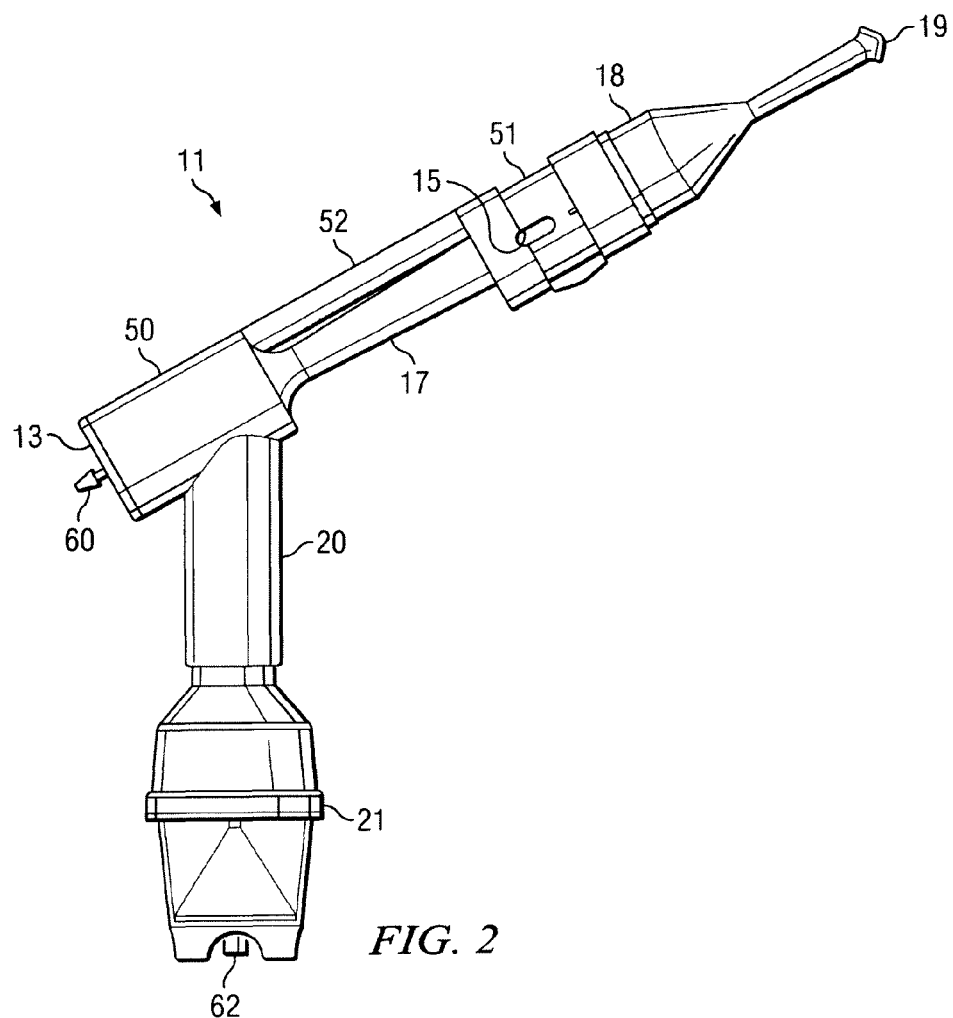
FIG. 2 is a side view of a patient interface device for use in connection with a continuous high-frequency oscillation breathing therapy system.
Figure 3:
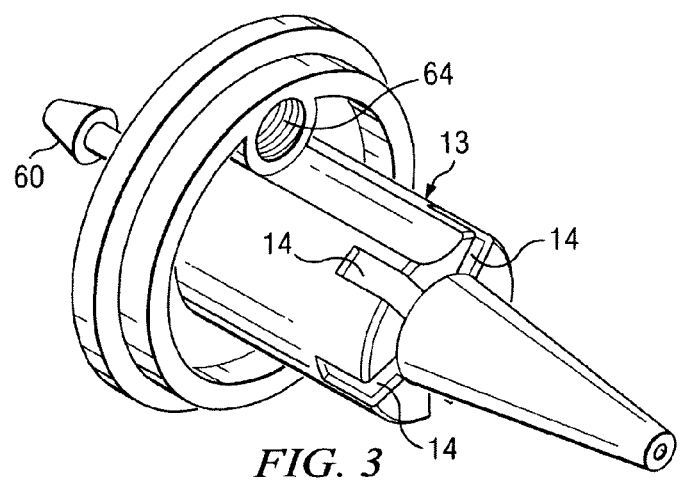
FIG. 3 is a perspective view of the injection nozzle of the present invention.
Figure 4:
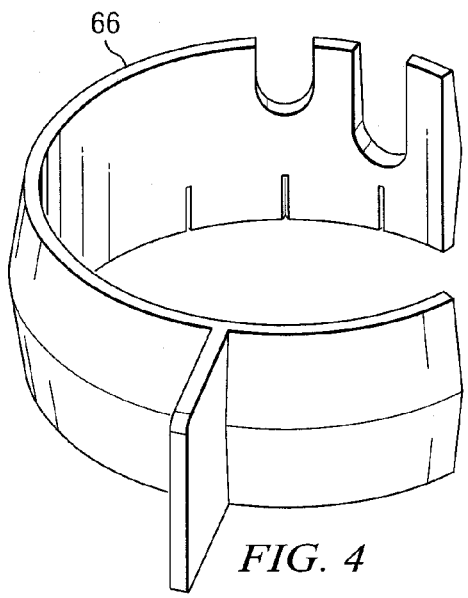
FIG. 4 is a front view of a rotatable occlusion collar.

FIG. 2 is a side view of the patient interface breathing head assembly 11 comprising injection nozzle 13, mouthpiece 18, nebulizer 21, pulsating gas input 60, nebulizer gas input 62 and pressure monitoring port 64 (see FIG. 3). In this embodiment, breathing head assembly 11 is shown having a rear cavity 50 associated with a front cavity 51 by means of venturi tube 17 and pressure monitoring port 64 associated with front cavity 51 by means of feedback tube 52. Mouthpiece 18 and mouthpiece opening 19 are removably attached to the front cavity 51 at the front end of breathing head assembly 11. Nebulizer 21 is removably attached to aerosol entrainment port 20. Aerosol entrainment port 20 is located toward the rear end of breathing head assembly 11, and operatively associated with rear cavity 50. The preferred embodiment allows for pieces to be removably attached, but any form of removable, permanent, or other type of attachment remains within the scope of the invention. As one having skill in the art will appreciate, many attachment means are known in the art and remain within the scope of the present invention.

Circuit tube 25 (FIG. 1) connects to nebulizer gas input 62 of nebulizer 21, which, in turn, connects to aerosol entrainment port 20 located at the rearmost portion of breathing head assembly 11. Circuit tube 10 (FIG. 1) connects to the rearmost end of breathing head assembly 11 by connecting directly to pulsating gas input 60 which feeds directly into injector nozzle 13. On the side wall of breathing head assembly 11 is at least one forward aperture 15 which opens the front cavity 51 of breathing head assembly 11 to the atmosphere. The forward portion of venturi tube 17 opens into front cavity 51. Feedback tube 52 comprises a first opening adjacent to the forward opening of venturi tube 17 and a second opening that is adjacent to rear cavity 50.

FIG. 3 shows an embodiment of injector nozzle 13, which is inserted into rear cavity 50 at the rear portion of breathing head assembly 11. Adjacent to injector nozzle 13 in this embodiment are a plurality of aft apertures 14 which open breathing head assembly 11 to the ambient. This figure also shows pulsating gas input 60 at the rear of injector nozzle 13.

Operation of the breathing treatment apparatus, pictured in FIGS. 1, 2 and 3, begins by loading a predetermined liquid medicament into nebulizer 21 by first detaching it from aerosol entrainment port 20. After filled nebulizer 21 is reattached, therapy is initiated by turning on source gas 1, which may be a compressor, or an external pressurized gas source such as air or oxygen. Gas travels through source gas supply tube 2 into pressure reduction regulator 3 whereby it is modulated to a suitable constant flow. In one embodiment, reduction regulator 3 can be pre-set at the factory to a desirable flow in order to maximize the simplicity of the therapy. The regulated gas then flows through tube 4 to splitting connector 5 which splits the gas into two streams. One goes into tube 22 where it may be further regulated by reducing orifice 23, and then continues to circuit connector 24. Circuit connector 24 connects circuit tube 25 which carries gas to the bottom of nebulizer 21. Nebulizer 21 converts the liquid medication into aerosol which enters into aerosol entrainment port 20, ushering the aerosol into rear cavity 50 of breathing head assembly 11.

Meanwhile, the other stream of gas that was split at splitting connector 5 continues into tube 6 and travels to flow interrupter valve 7. Valve 7 chops the constant gas flow into high-frequency pulses by interrupting it at regular intervals so that the flow becomes divided into substantially equal volumes, or pulses, preferably at a rate of 1 to 15 hertz. In one embodiment, valve 7 can be pre-set to a specific rate to maximize the simplicity of the therapy. Because the flow is constant and the pulses are substantially equal, the resulting pulsatile pressure amplitude is substantially constant. That is to say that the difference between the lowest pressure and the highest pressure of each pulse is substantially equal.

The high-frequency flow then continues through circuit 8 to circuit connector 9. Circuit connector 9 connects circuit tube 10 which carries the gas to pulsating gas input 60. As will be appreciated by one having skill in the art, circuit connectors may be eliminated by connecting directly into the gas inputs or exhausts and will remain within the scope of the invention. Here, the high-frequency pulses enter injector nozzle 13 which directs them into the rear opening of venturi tube 17. Simultaneously, the increased velocity resulting from the narrowing of injector nozzle 13 lowers surrounding pressures creating a vacuum effect, first described by Swiss mathematician Daniel Bernoulli in 1738, pulling in or entraining additional gas as well as medicament from nebulizer 21. Second, the friction between the high speed molecules and the adjacent low-speed molecules has the effect of pulling the low-speed gas molecules into the stream of the high speed gas.

In effect, ambient gas is pulled into the rear cavity of breathing head assembly 11 through aft apertures 14 and aerosol entrainment port 20. As the velocity of the gas increases, the volume of entrained gas increases, and, therefore, overall flow increases.

The continuous high-frequency pulsatile flow enters into venturi tube 17 which may either amplify or attenuate it. As the flow enters venturi tube 17, given little or no resistance at mouthpiece opening 19, the flow is amplified. However, as resistance at mouthpiece opening 19 increases, such as would result from the backpressure caused by a patient exhaling into mouthpiece opening 19, the entrainment process is impeded and overall flow is attenuated. Velocity within the venturi decreases, and, in turn, entrainment and flow both decrease. Thus, the device allows the patient to exhale back into it, and the device is provided with a built-in safety mechanism. As the patient exhales or airway compliance decreases, resistance downstream from the venturi tube increases. The resulting decrease in delivered flow also decreases pressure, thereby protecting the airways and allowing the patient to exhale.

The mixture of high-frequency pulsatile flow from injection nozzle 13, aerosol from port 20, and ambient air from aft entrainment apertures 14 continue through the lumen of venturi tube 17, exiting its forward opening into mouthpiece 18 and out mouthpiece opening 19 to the patient. The patient seals his or her lips around mouthpiece 18 and inhales the aerosolized pulses of gas, taking them deep into the lungs. The patient then exhales back into mouthpiece opening 19 as the therapy continues. The combination of aft apertures 14 and forward aperture 15 allow both ingress and egress of flow, serving both inhalation and exhalation without the need for complex mechanisms to open and close valves during the therapy.

As the patient continues the high-frequency oscillation breathing therapy, several processes may begin. The medicated aerosol and the oscillation of the air column in the conducting airways may help reduce viscosity of the secretions. The bi-level flow created by high-frequency intermittent delivery of gas may also begin to create wind shear forces. Specifically, during the therapy a small pulse enters the airways, and then the flow momentarily stops. During this pause, the pressure in the upper airways drops. Small volumes of gas that were previously delivered into the airways now begin to exit, momentarily unencumbered by the low pressure condition in the upper airways. As these exiting volumes of gas increase in velocity they continually push secretions from small distal airways to the larger openings in the upper airways where they can be more easily removed.

Throughout the high-frequency oscillation therapy session, the intermittent positive-pressure pulses continue as the patient inhales and exhales through mouthpiece opening 19. The exhaled breath travels from mouthpiece opening 19 into front cavity 51 and exits forward aperture 15. Aft apertures 14 and forward aperture 15 are calibrated with flow interrupter 7 so that the patient is able to exhale back into mouthpiece opening 19 even as the high-frequency positive gas flow continues. This calibration allows ample opportunity for exhaled breath to escape in order to prevent the successive stacking of inhaled breaths in the airways.

During the high-frequency oscillation therapy session, the patient's lung pressure may be monitored by attaching a pressure sensor such as a manometer to pressure monitoring port 64 which is associated with the second opening of feedback tube 52. The first opening of feedback tube 52 opens into front cavity 51 and is operatively associated with mouthpiece 18 to improve lung pressure monitoring. The preferred embodiment is shown with feedback tube 52 having a first opening near mouthpiece 18 to improve the accuracy of the pressure reading and a second opening adjacent to rear cavity 50 to improve the ease of patient handling. As one skilled in the art will appreciate, other positions of a feedback tube may be employed and the feedback tube may be used as a connecting piece and still remain within the scope of the invention.

FIG. 4 shows rotatable occlusion collar 66. Collar 66 may be placed over forward aperture 15 (FIG. 2) to partially occlude forward aperture 15 and effect the ingress and egress of air from front cavity 51 (FIG. 2). The rotation of collar 66 may be used to allow a variable occlusion to occur over forward aperture 15 depending on the amount of rotation.

FIG. 5 presents an alternate embodiment exploded sectional view of forward aperture 15 of breathing head assembly 11 with an annular aperture adjustment collar 31 to provide a means for partially occluding aperture 15 in order to increase and decrease the ingress and egress of flow. In this embodiment, each of aperture adjustment collar holes 32 is surrounded by a safety crown 33 to prevent inadvertent complete occlusion.

Aperture adjustment collar 31 is slidably attached to breathing head assembly 11 adjacent to forward aperture 15 so that it can be axially adjusted. When aperture adjustment collar 31 is positioned so that aperture adjustment holes 32 align fully with forward aperture 15, maximum ingress and egress of flow is allowed. As aperture adjustment collar 31 is rotated so that aperture adjustment holes 32 begin to overlap forward apertures 15, effectively reducing the opening size of the apertures, ingress and egress of flow becomes more diminished. The peaks of safety crown 33 eliminate inadvertent complete occlusion of aperture adjustment collar holes 32 by preventing a finger or hand from sealing them. The embodiment depicted in FIG. 5 is shown as applied to forward aperture 15, which may be designated as primary for egress of flow. However, the adjustment collar 31 depicted in FIG. 5 may also be applied to aft apertures 14, which may be designated as primary for ingress of flow.

FIG. 6 is a schematic diagram of an alternate embodiment that includes a number of additional features incorporated into the continuous high-frequency oscillation breathing treatment device. Timer 34 is connected to source gas 1, as is patient compliance monitor 35 and RFID transceiver 42. Reservoir splitter 36 connects tube 37 to tube 22. Tube 37 connects by the other end to medicament reservoir 38. Medicament reservoir 38 is in communication with nebulizer 21 via tube 39. Specified gas source 40 connects to one end of inspiratory gas connector 41. The other end of inspiratory gas connector 41 connects to aft apertures 14. RFID tag 43 is embedded into a plastic wall of nebulizer 21. Evacuation reservoir 49 connects to forward apertures 15 by means of evacuation reservoir tube 48.

Timer 34 allows the clinician or the patient to pre-set a time for the treatment. At the end of the therapy session timer 34 can either turn off the apparatus by terminating source gas 1, or sound an alarm to notify the patient that the treatment is over. Patient compliance monitor 35 logs use of the device in order to allow a clinician to determine whether or not the patient is utilizing the device. Medicament Reservoir 38 receives gas flow through tube 37, which is connected to tube 22 by reservoir splitter 36. Medication is delivered from medicament reservoir 38 through tube 39 to nebulizer 21. This allows medication to be stored in a location remote from nebulizer 21, and medication can be continually pumped into nebulizer 21 as the therapy progresses.

Aft apertures 14 may be designated as primary for inspiration. In this case, the content of inspired gas can be controlled by connecting specified gas source 40 to aft apertures 14 by way of inspiratory gas connector 41. Forward apertures 15 may be designated as primary for exhalation. In this case, apertures 15 can be left open to the ambient or can be connected to evacuation reservoir 49. RFID (Radio Frequency Identification) transceiver 42, connected to source gas 1, can recognize identification information transmitted from RFID tag 43, embedded in nebulizer 21, to determine whether or not the component is compatible with the apparatus. RFID transceiver 42 can be programmed to prevent gas source 1 from being initiated if a component is incompatible.

Figure 7:
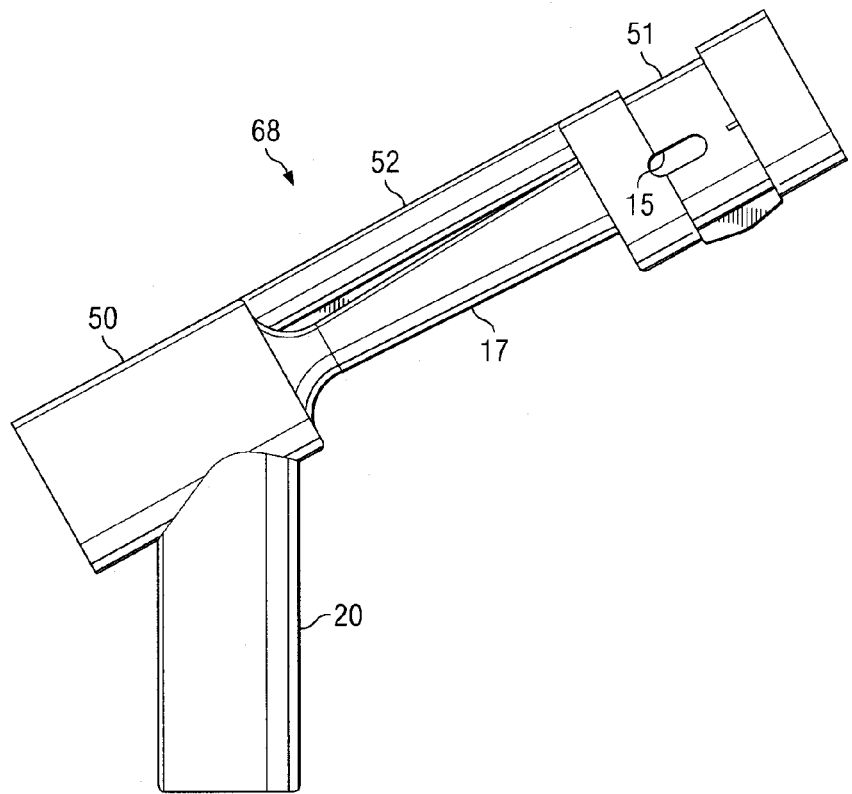
FIG. 7 is a side view of the body of the patient interface device made from unitary construction.
Figure 5:
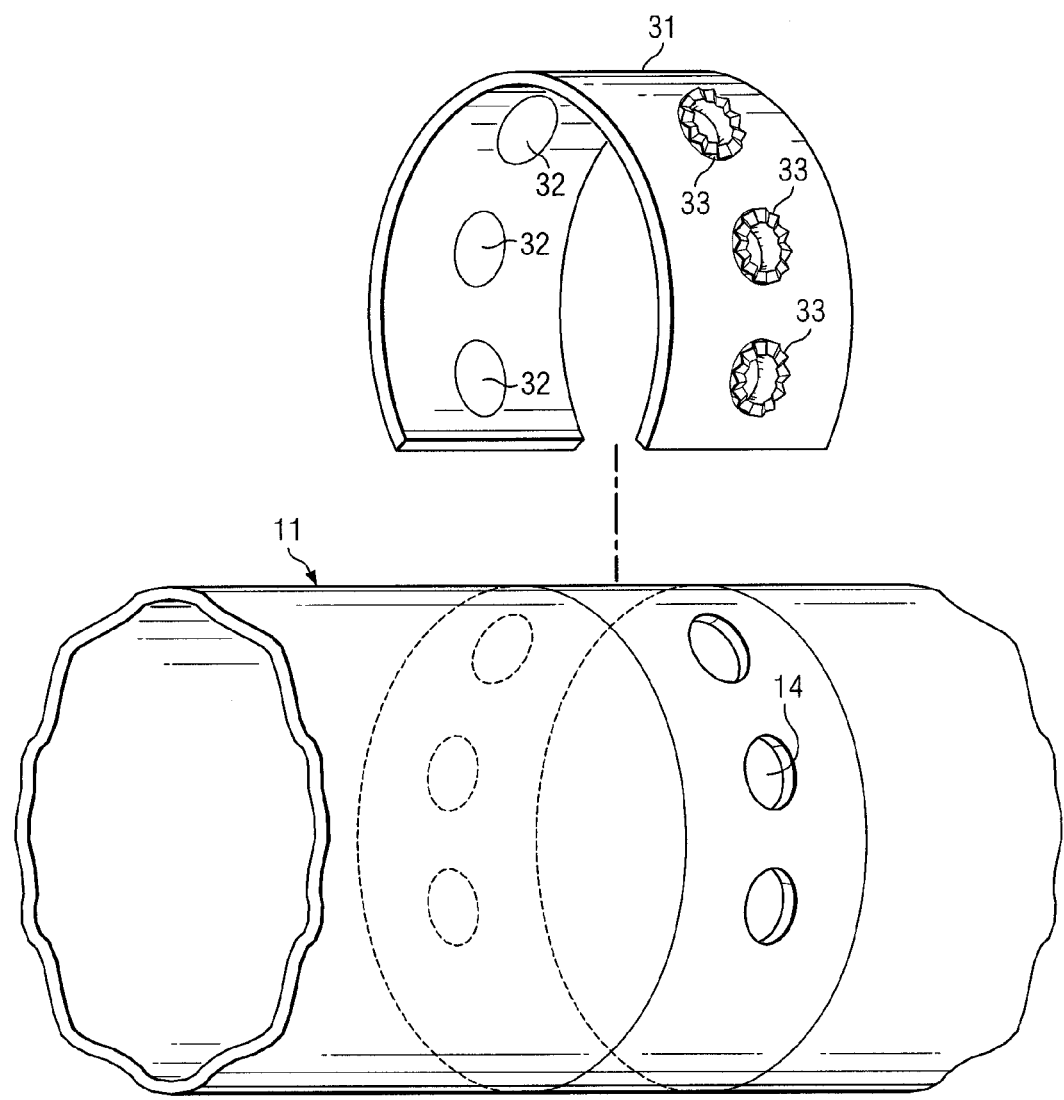
FIG. 5 is an alternate embodiment exploded sectional view of the forward apertures of the patient interface with a means for their partial occlusion, and a means to prevent inadvertent complete occlusion of the apertures.
Figure 6:
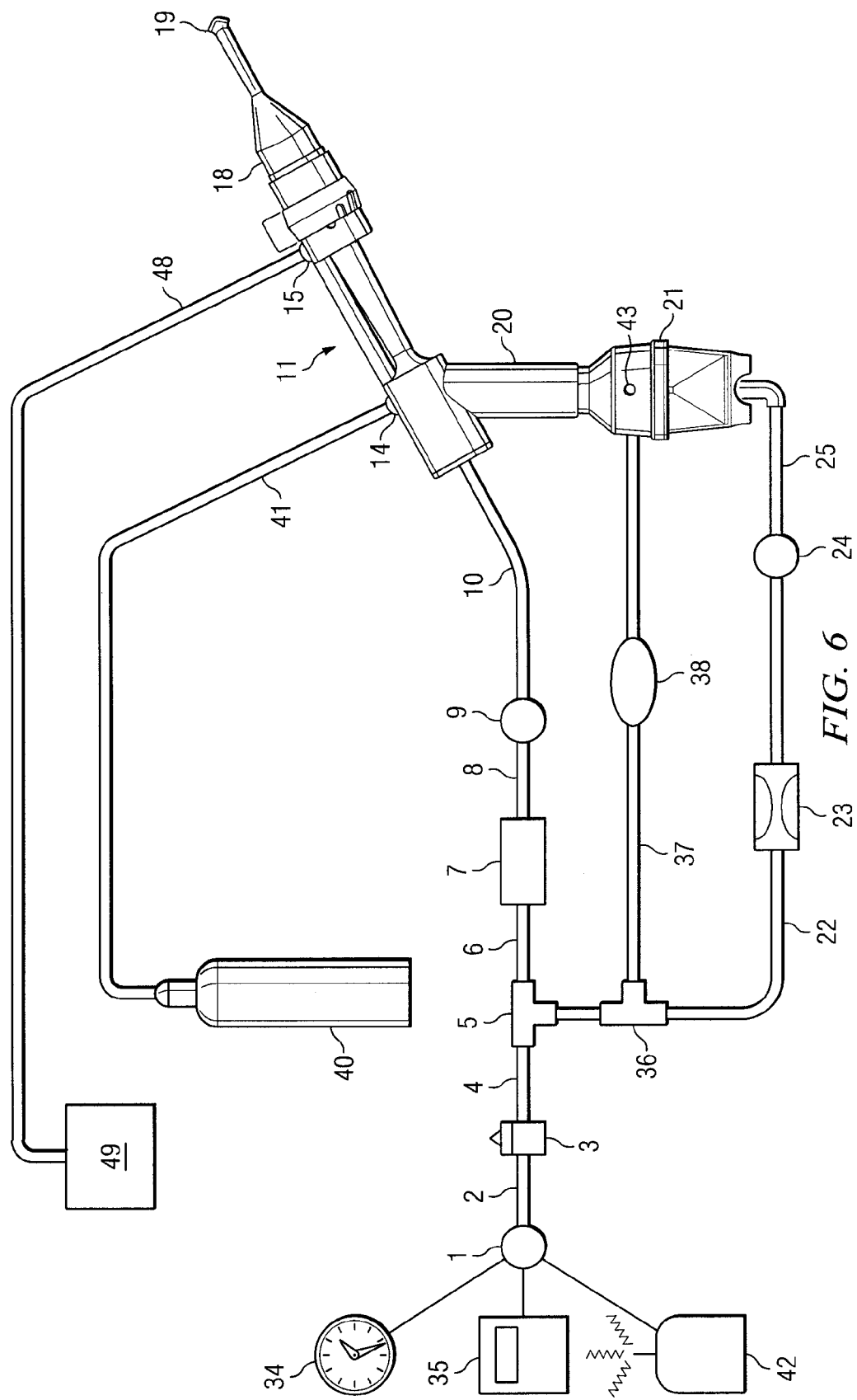
FIG. 6 is a schematic representation of an alternate embodiment of the continuous high-frequency oscillation breathing therapy apparatus of present invention.

FIG. 7 shows body 68 of breathing head assembly 11. Body 68 is made of a unitary construction and incorporates a first cavity, which in the embodiment shown is front cavity 51, a second cavity, which in the embodiment shown is rear cavity 50, a first passageway, which in the embodiment shown is venturi tube 17, a second passageway, which in the embodiment shown is feedback tube 52, forward aperture 15, and entrainment cavity 20. Unitary construction is a preferred embodiment for the invention, but as will be appreciated by one having skill in the art, unitary construction is not necessary and other forms of construction are within the scope and spirit of the invention.

What is claimed is:

1. A continuous high-frequency oscillation breathing treatment apparatus comprising:
   a breathing head assembly defining a first cavity, a second cavity spaced from the first cavity, a pressure monitoring port, and an entrainment cavity, wherein said first cavity is operatively associated with said second cavity through a venturi tube, said first cavity is operatively associated with said pressure monitoring port through a feedback tube that extends generally parallel with the venturi tube, and said entrainment cavity is operatively associated with said second cavity;
   a nebulizer operatively associated with said entrainment cavity of said breathing head assembly;
   an injection nozzle operatively associated with said second cavity of said breathing head assembly;
   at least one first aperture operatively associated with said first cavity of said breathing head assembly;
   a plurality of second apertures operatively associated with said second cavity of said breathing head assembly;
   at least one gas input operatively associated with said nebulizer; and
   at least one gas input operatively associated with said injection nozzle.

2. The apparatus of claim 1 wherein at least one of said second apertures is integrated with said injection nozzle.

3. The apparatus of claim 1 wherein said at least one first aperture may be partially occluded.

4. The apparatus of claim 3 further comprising a rotatable occlusion apparatus.

5. The apparatus of claim 4 wherein said rotatable occlusion apparatus varies the area of said at least one first aperture occluded as it rotates.

6. The apparatus of claim 1 wherein said pressure monitoring port is provided as part of said injection nozzle.

7. The apparatus of claim 1 further comprising a means of pulsating a gas flow operatively associated with said injection nozzle.

8. The apparatus of claim 7 wherein said at least one gas input operatively associated said injection nozzle is operatively associated with said injection nozzle through said means of pulsating a gas flow.

9. A continuous high-frequency oscillation breathing treatment apparatus comprising:
   a breathing head assembly of unitary construction defining a first cavity, a second cavity spaced from the first cavity, a pressure monitoring port, and an entrainment cavity, wherein said first cavity is operatively associated with said second cavity through a venturi tube, said first cavity is operatively associated with said pressure monitoring port through a feedback tube that extends generally parallel with the venturi tube, and said entrainment cavity is operatively associated with said second cavity;
   a nebulizer operatively associated with said entrainment cavity of said breathing head assembly;
   an injection nozzle operatively associated with said second cavity of said breathing head assembly;
   at least one first aperture operatively associated with said first cavity of said breathing head assembly;
   a plurality of second apertures operatively associated with said second cavity of said breathing head assembly;
   at least one gas input operatively associated with said nebulizer; and
   at least one gas input operatively associated with said injection nozzle.

10. The apparatus of claim 9 wherein at least one of said second apertures is adjacent to said injection nozzle.

11. The apparatus of claim 9 wherein said at least one first aperture may be partially occluded.

12. The apparatus of claim 11 further comprising a rotatable occlusion apparatus.

13. The apparatus of claim 12 wherein said rotatable occlusion apparatus varies the area of said at least one first aperture occluded as it rotates.

14. The apparatus of claim 12 wherein said pressure monitoring port is provided as part of said injection nozzle.

15. The apparatus of claim 9 further comprising a means of pulsating a gas flow operatively associated with said injection nozzle.

16. The apparatus of claim 15 wherein said at least one gas input operatively associated with said injection nozzle is operatively associated with said injection nozzle through said means of pulsating a gas flow.

* * * * *